(12) United States Patent
Kaneko et al.

(10) Patent No.: US 11,578,310 B2
(45) Date of Patent: Feb. 14, 2023

(54) METHOD FOR PRODUCING CD4/CD8 DOUBLE-POSITIVE T CELLS

(71) Applicant: Kyoto University, Kyoto (JP)

(72) Inventors: Shin Kaneko, Kyoto (JP); Yutaka Yasui, Kyoto (JP); Shoichi Iriguchi, Kyoto (JP); Tatsuki Ueda, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 662 days.

(21) Appl. No.: 16/312,789

(22) PCT Filed: Jun. 21, 2017

(86) PCT No.: PCT/JP2017/022840
§ 371 (c)(1),
(2) Date: Dec. 21, 2018

(87) PCT Pub. No.: WO2017/221975
PCT Pub. Date: Dec. 28, 2017

(65) Prior Publication Data
US 2019/0330596 A1 Oct. 31, 2019

(30) Foreign Application Priority Data
Jun. 23, 2016 (JP) .............................. JP2016-124924

(51) Int. Cl.
| | |
|---|---|
| C12N 5/074 | (2010.01) |
| C07D 401/04 | (2006.01) |
| C07K 14/725 | (2006.01) |
| C12N 5/0783 | (2010.01) |
| C12N 5/10 | (2006.01) |
| C12N 15/85 | (2006.01) |

(52) U.S. Cl.
CPC ......... *C12N 5/0696* (2013.01); *C07D 401/04* (2013.01); *C07K 14/7051* (2013.01); *C12N 5/0636* (2013.01); *C12N 5/10* (2013.01); *C12N 15/85* (2013.01); *C12N 2501/21* (2013.01); *C12N 2506/03* (2013.01); *C12N 2506/45* (2013.01); *C12N 2510/00* (2013.01)

(58) Field of Classification Search
CPC . C12N 5/0636; C12N 2506/45; C12N 5/0696
USPC ....................................................... 435/377
See application file for complete search history.

(56) References Cited

U.S. PATENT DOCUMENTS

| | | |
|---|---|---|
| 2013/0078226 A1 | 3/2013 | Nakauchi et al. |
| 2017/0326175 A1 | 11/2017 | Kaneko |
| 2018/0298337 A1 | 10/2018 | Kaneko |

FOREIGN PATENT DOCUMENTS

WO WO 2016/076415 A1 5/2016

OTHER PUBLICATIONS

Iriguchi (2021, Nature Communications, 12:430, pp. 1-15).*
Wang (2006, Exp Hematol, 34:1730-1740).*
Ara, et al. 2003 "A role of CXC chemokine ligand 12/stromal cell-derived factor-1/pre-b cell growth stimulating factor and its receptor CXCR4 in fetal and adult T cell development in vivo" *The Journal of Immunology* 170: 4649-4655.
Fernandez 2000 "Thymocyte development past the $CD4^+CD8^+$ stage requires an active p38 mitogen-activated protein kinase" *Blood* 95(4): 1356-1361.
Gattinoni, et al. 2006 "Adoptive immunotherapy for cancer: building on success" *Nature Review: Immunology* 6(5): 383-393.
Ikawa, et al. 2010 "An essential developmental checkpoint for productions of the T cell lineage" *Science* 329: 93-96.
International Search Report for International Application No. PCT/JP2017/022840 dated Sep. 19, 2017 in 2 pages.
Nishimura, et al. 2013 "Generation of Rejuvenated Antigen-Specific T Cells by Reprogramming to Pluripotency and Redifferentiation" *Cell Stem Cell* 12: 114-126.
Morgan, et al. 2006 "Cancer regression in patients after transfer of genetically engineered lymphocytes" *Science* 314: 126-129.
Mulroy & Sen 2001 "p38 MAP kinase activity modulates $\alpha\beta$ T cell development" *Eur. J. Immunol* 31: 3056-3063.
Rincon & Pedraza-Alva 2003 "JNK and P38 Map kinases in $CD4^+$ and $CD8^+$ T cells" *Immunological Reviews* 192: 131-142.
Takayama, et al. 2008 "Generation of functional platelets from human embryonic stem cells in vitro via ES-sacs, VEGF-promoted structures that concentrate hematopoietic progenitors" *Blood* 111(11): 5298-5306.
Timmermans, et al. 2009 "Generation of T Cells from Human Embryonic Stem Cell-Derived Hematopoietic Zones¹" *The Journal of Immunology* 182(11): 6879-6888.
Yanagawa, et al. 2001 "Enhancement of stromal cell-derived factor-$1\alpha$-induced chemotaxis for CD4/8 double-positive thymocytes by fibronectin and laminin in mice" *Immunology* 104: 43-49.
International Preliminary Report on Patentability, dated Jan. 3, 2019, International Patent Application No. PCT/JP2017/022840.
Gattinoni, L., et al., Adoptive immunotherapy for cancer: building on success, Nature Reviews: Immunology, vol. 6, pp. 383-393, 2006.
Ikawa, T., et al., An essential developmental checkpoint for production of the T cell lineage, Science vol. 329, pp. 93-96, 2010.
Zou, J., et al. Inhibition of p38 MAPK activity promotes ex vivo expansion of human cord blood hematopoietic stem cells, Annals of Hematology, vol. 91, No. 6, pp. 813-823, 2012.
Extended European Search Report, dated Jan. 27, 2020, issued in European Application No. 17815443.1.
Diehl, N.L., et al., Activation of the p38 Mitogen-activated Protein Kinase Pathway Arrests Cell Cycle Progression and Differentiation of Immature Thymocytes In Vivo, *Journal of Experimental Medicine*, vol. 191, No. 2, pp. 321-334, 2000.

(Continued)

*Primary Examiner* — Valarie E Bertoglio
(74) *Attorney, Agent, or Firm* — Knobbe, Martens, Olson & Bear LLP

(57) ABSTRACT

A method for producing CD4/CD8 double-positive T cells, comprising the steps of: (1) culturing pluripotent stem cells in a medium to induce hematopoietic progenitor cells; and (2) culturing the hematopoietic progenitor cells obtained in the step (1) in a medium containing a p38 inhibitor and/or SDF-1 to induce CD4/CD8 double-positive T cells.

16 Claims, 11 Drawing Sheets

(56) References Cited

OTHER PUBLICATIONS

Koprak, S., et al., A Specific Inhibitor of the p38 Mitogen Activated Protein Kinase Affects Differentially the Production of Various Cytokines by Activated Human T Cells: Dependence on CD28 Signaling and Preferential Inhibition of IL-10 Production, *Cellular Immunology*, vol. 192, No. 2, pp. 87-95, 1999.

Wang et al., Inhibition of p38 mitogen-activated protein kinase promotes ex vivo hematopoietic stem cell expansion, Stem Cells and Development, vol. 20, No. 7, 1143-1152, 2011.

Office Action dated Jul. 18, 2022 in Chinese Application No. 201780039329.0.

Suzuki et al., Diverse Transcriptional Response of CD4+ T Cells to Stromal Cell-Derived Factor (SDF)-1: Cell Survival Promotion and Priming Effects of Sdf-1 on CD4+ T Cells, The Journal of Immunology, vol. 167, pp. 3064-3073, 2001.

\* cited by examiner

METHOD FOR PRODUCING CD4/CD8 DOUBLE-POSITIVE T CELLS

TECHNICAL FIELD

The present invention relates to a method for producing CD4/CD8 double-positive T cells from hematopoietic progenitor cells, a method for producing CD4/CD8 double-positive T cells from pluripotent stem cells, and a method for producing CD8-positive T cells from the CD4/CD8 double-positive T cells.

BACKGROUND ART

T cells play a central role in the immune system against foreign pathogens such as bacteria and viruses, and against abnormal cells such as cancer cells. It is thought that a decrease in the function of T cells due to various causes may lead to increased susceptibility to infection and development of cancer and the like. If replacement or regeneration of immune cells is possible in cases of such diseases, it may act as very effective means for amelioration of the disease state and improvement of a therapeutic effect on the diseases. In such a replacement therapy of immune cells, replacement and regeneration of the function of T lymphocytes, which are responsible for cell-mediated immunity, have been strongly demanded. However, no effective therapeutic method has been established so far.

In such replacement therapies of T lymphocytes that have been proposed, gene transfer of an antigen-specific T cell receptor (TCR) gene into various lymphoid cells is carried out to allow replacement and activation of specific immune reaction (Non-patent Documents 1 and 2). In these attempts, CD34-positive cells, which are bone marrow progenitor cells, naive T lymphocytes, and the like are used as the cells to be subjected to the gene transfer. However, these have a number of disadvantages such as low ability of ex-vivo self-renewal, low gene transfer efficiency, and difficulty in regulation of differentiation by gene transfer.

Replacement therapies using T lymphocytes induced from pluripotent stem cells such as iPS cells have also been proposed (Non-patent Document 3 and Patent Document 1). In the method for inducing T lymphocytes from pluripotent stem cells, (1) a step of inducing hematopoietic progenitor cells from pluripotent stem cells, (2) a step of inducing CD4/CD8 double-negative cells from the hematopoietic progenitor cells, (3) a step of inducing CD4/CD8 double-positive cells from the CD4/CD8 double-negative cells, and (4) a step of inducing T lymphocytes from the CD4/CD8 double-positive cells, have been proposed.

For the step (1), a method in which a net-like structure sac (ES-sac) is formed from pluripotent stem cells to produce hematopoietic progenitor cells is known (Non-patent Document 4). For the steps (2) and (3), methods in which culture is performed on an OP9-DL1 cell layer in a medium supplemented with IL-7 and Flt-3L are known (Non-patent Documents 5 and 6). For the step (4), a method in which culture is performed in a medium supplemented with an anti-CD3 antibody (OKT-3) and IL-2 is known.

Patent Document 2 discloses a method for producing CD4/CD8 double-positive T cells from pluripotent stem cells using a medium supplemented with vitamin C.

However, the efficiencies of production of T lymphocytes from pluripotent stem cells in these methods are insufficient, and their improvement has been demanded.

PRIOR ART DOCUMENTS

Patent Documents

Patent Document 1: WO 2011/096482
Patent Document 2: WO 2016/076415

Non-Patent Documents

Non-patent Document 1: Gattinoni L, et al., Nat Rev Immunol. 6(5): 383-393, 2006
Non-patent Document 2: Morgan R A, et al., Science. 314(5796): 126-129, 2006
Non-patent Document 3: Nishimura T, et al., Cell Stem Cell. 12(1): 114-126, 2013.
Non-patent Document 4: Takayama N. et al., Blood. 111 (11): 5298-5306, 2008
Non-patent Document 5: Timmermans F, et al., J Immunol. 182(11): 6879-6888, 2009
Non-patent Document 6: Ikawa T, et al., Science. 329(5987): 93-96, 2010

SUMMARY OF THE INVENTION

An object of the present invention is to produce CD4/CD8 double-positive T cells efficiently from hematopoietic progenitor cells, and to produce CD4/CD8 double-positive T cells efficiently from pluripotent stem cells.

In order to achieve the above object, the present inventors searched for substances that are effective for efficient induction of CD4/CD8 double-positive T cells from hematopoietic progenitor cells. As a result, the present inventors discovered that CD4/CD8 double-positive T cells can be efficiently induced by culturing hematopoietic progenitor cells in a medium supplemented with a p38 inhibitor and/or SDF-1, thereby completed the present invention.

More specifically, the present invention provides the following inventions.

[1] A method for producing CD4/CD8 double-positive T cells, the method comprising the step of culturing hematopoietic progenitor cells in a medium containing a p38 inhibitor and/or SDF-1 to induce CD4/CD8 double-positive T cells.
[2] The method according to [1], wherein the medium contains a p38 inhibitor and SDF-1.
[3] The method according to [1] or [2], wherein the p38 inhibitor is SB203580.
[4] The method according to any one of [1] to [3], wherein, in the step, the medium contains vitamin C.
[5] The method according to any one of [1] to [4], wherein the step is carried out by adherent culture.
[6] The method according to any one of [1] to [5], wherein the hematopoietic progenitor cells are cultured without using feeder cells.
[7] The method according to any one of [1] to [6], wherein the hematopoietic progenitor cells are hematopoietic progenitor cells differentiated from pluripotent stem cells.
[8] The method according to [7], wherein the pluripotent stem cells are induced pluripotent stem cells.
[9] The method according to [8], wherein the induced pluripotent stem cells are derived from somatic cells other than T cells.
[10] The method according to [8] or [9], wherein the induced pluripotent stem cells are induced pluripotent stem cells having a chimeric antigen receptor introduced therein.
[11] A method for producing CD4/CD8 double-positive T cells, comprising the steps of:

(1) culturing pluripotent stem cells in a medium to induce hematopoietic progenitor cells; and
(2) culturing the hematopoietic progenitor cells obtained in the step (1) in a medium containing a p38 inhibitor and/or SDF-1 to induce CD4/CD8 double-positive T cells.

[12] The method according to [11], wherein, in the step (2), the medium contains a p38 inhibitor and SDF-1.

[13] The method according to [11] or [12], wherein the p38 inhibitor is SB203580.

[14] The method according to any one of [11] to [13], wherein the step (1) is carried out by suspension culture.

[15] The method according to any one of [11] to [14], wherein the step (2) is carried out by adherent culture.

[16] The method according to any one of [11] to [15], wherein, in the steps (1) and (2), the medium contains vitamin C.

[17] The method according to any one of [11] to [16], wherein, in the steps (1) and (2), the culture is carried out without using feeder cells.

[18] The method according to any one of [11] to [17], wherein the pluripotent stem cells are induced pluripotent stem cells.

[19] The method according to [18], wherein the induced pluripotent stem cells are derived from somatic cells other than T cells.

[20] The method according to [18] or [19], wherein the induced pluripotent stem cells are induced pluripotent stem cells having a chimeric antigen receptor introduced therein.

[21] A method for producing CD8-positive T cells, comprising the steps of: producing CD4/CD8 double-positive T cells by the method according to any one of [1] to [20]; and culturing the obtained CD4/CD8 double-positive T cells in a medium supplemented with an adrenocortical hormone agent to obtain CD8-positive T cells.

[22] A cell preparation comprising CD4/CD8 double-positive T cells obtained by the method according to any one of [1] to [20] and/or CD8-positive T cells obtained by the method according to [21].

Effect of the Invention

According to the present invention, CD4/CD8-positive T cells can be efficiently produced from hematopoietic progenitor cells. Further, CD4/CD8-positive T cells can be efficiently produced from pluripotent stem cells. Further, by addition of an adrenocortical hormone agent to the medium, CD8-positive T cells can be efficiently produced from CD4/CD8 double-positive T cells.

EMBODIMENTS FOR CARRYING OUT THE INVENTION

Figure 1:
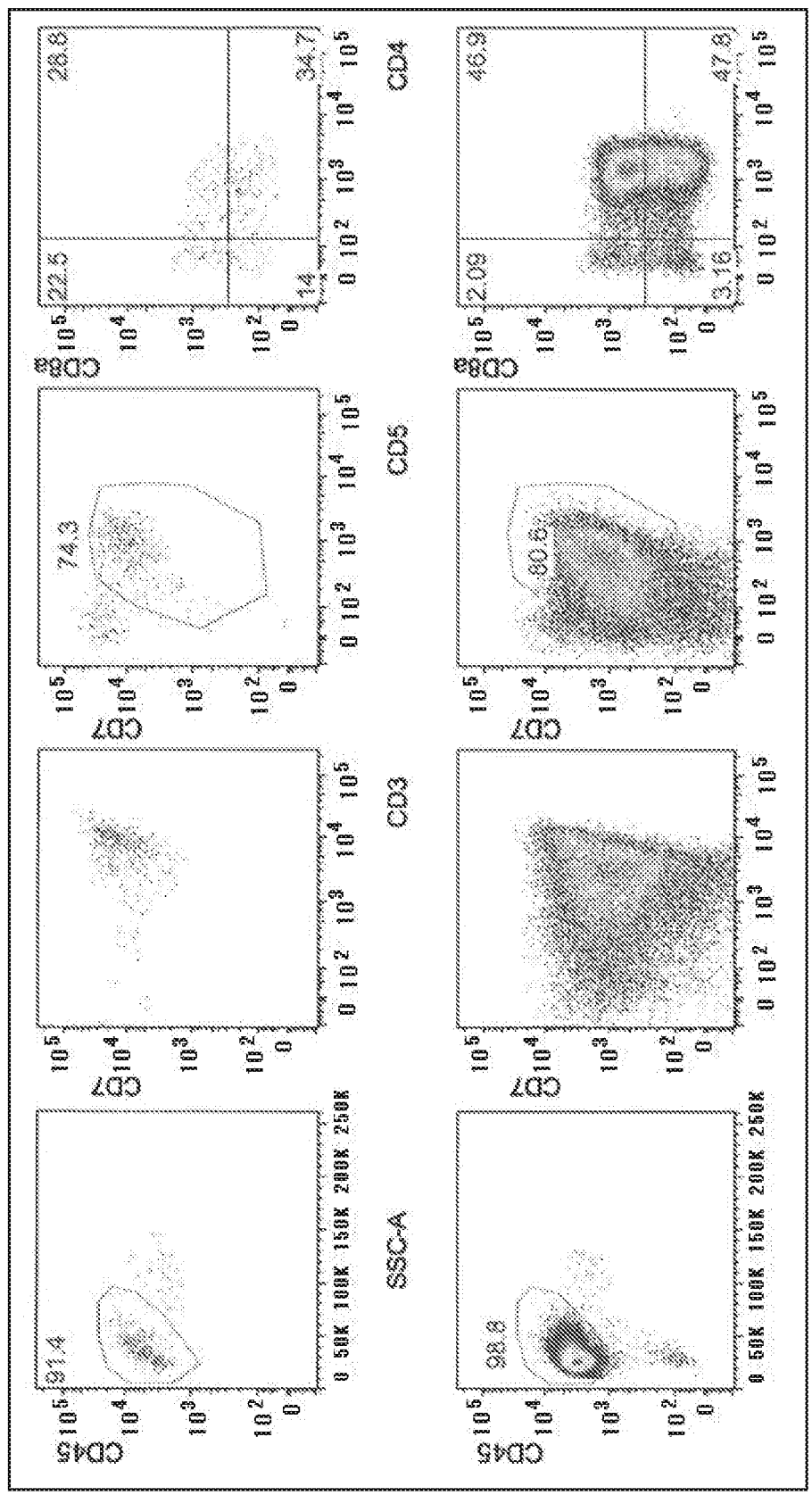
FIG. 1 shows the results of flow cytometry of cells obtained by differentiation induction from iPS cells (TkT3V1-7). From left to right, diagrams developed for the staining intensities of CD45 and SSC, diagrams developed for the staining intensities of CD7 and CD3, diagrams developed for the staining intensities of CD7 and CD5, and diagrams developed for the staining intensities of CD8 and CD4 are shown. The top row shows the results obtained for a case where neither SB203580 nor SDF-1α was added, and the bottom row shows the results obtained for a case where SB203580 and SDF-1α were added.

The present invention provides a method for producing CD4/CD8 double-positive T cells from hematopoietic progenitor cells.

Step of Inducing CD4/CD8 Double-Positive T Cells from Hematopoietic Progenitor Cells In the present invention, the hematopoietic progenitor cells (HPCs) are cells that are capable of differentiation into blood cells such as lymphocytes, eosinophils, neutrophils, basophils, erythrocytes, and megakaryocytes. In the present invention, hematopoietic progenitor cells and hematopoietic stem cells are not distinguished from each other, and are regarded as the same kind of cells unless otherwise specified. The hematopoietic stem cells/progenitor cells can be recognized based on, for example, the positivity of CD34 and/or CD43, which are surface antigens.

As the hematopoietic progenitor cells, hematopoietic progenitor cells induced from pluripotent stem cells as described later may be used, or hematopoietic progenitor cells obtained by another method, such as CD34-positive cells derived from cord blood, may be used.

In the present invention, the "CD4/CD8 double-positive T cells" means T cells positive for both of the surface antigens CD4 and CD8 ($CD8^+CD4^+$). Since T cells can be recognized by the fact that they are positive for the surface antigens CD3 and CD45, CD4/CD8 double-positive T cells can be identified as cells positive for CD4, CD8, CD3, and CD45. CD4/CD8 double-positive T cells can be induced to differentiate into CD4-positive cells or CD8-positive cells.

In the present invention, the CD4/CD8 double-positive T cells can be produced by a method comprising a step of culturing hematopoietic progenitor cells in a medium supplemented with a p38 inhibitor and/or SDF-1.

<p38 Inhibitor>

The "p38 inhibitor" according to the present description is defined as a substance which inhibits the function of p38 protein (p38 MAP kinase), and examples thereof include, but are not limited to, chemical inhibitors of p38, and dominant negative mutants of p38 and nucleic acids encoding them.

Examples of the chemical inhibitors of p38 in the present invention include, but are not limited to, SB203580 (4-(4-fluorophenyl)-2-(4-methylsulfonylphenyl)-5-(4-pyridyl)-1H-imidazole) and derivatives thereof; SB202190 (4-(4-fluorophenyl)-2-(4-hydroxyphenyl)-5-(4-pyridyl)-1H-imidazole) and derivatives thereof; SB239063 (trans-4-[4-(4-fluorophenyl)-5-(2-methoxy-4-pyrimidinyl)-1H-imidazol-1-yl]cyclohexanol) and derivatives thereof; SB220025 and derivatives thereof; PD169316; RPR200765A; AMG-548; BIRB-796; SCIO-469; SCIO-323; VX-702; and FR167653. These compounds are commercially available, and, for example, SB203580. SB202190, SC239063, SB220025, and PD169316 are available from Calbiochem; and SCIO-469 and SCIO-323 are available from Scios and the like.

Examples of the dominant negative mutants of p38 include p38T180A, wherein the threonine at position 180 located in the DNA-binding region of p38 is substituted with alanine by point mutation; and p38Y 182F, wherein the tyrosine at position 182 of p38 in human and mouse is substituted with phenylalanine by point mutation.

The p38 inhibitor is contained in the medium at, for example, about 1 µM to about 50 µM.

<SDF-1>

In the present invention, the SDF-1 (Stromal cell-derived factor 1) is not limited to SDF-1α or a mature type thereof, and may be an isoform such as SDF-1β, SDF-1γ, SDF-1δ, SDF-1ε, or SDF-1φ, or a mature type thereof. The SDF-1 may also be a mixture or the like containing these at arbitrary ratios. SDF-1α is preferably used. SDF-1 may also be referred to as CXCL-12 or PBSF.

In the present invention, the SDF-1 may have an amino acid sequence having substitution, deletion, and/or addition of one or several amino acid(s), or may similarly have substitution, deletion, and/or addition of a sugar chain(s), as long as the activity as a chemokine is retained. An amino acid mutation(s) is/are acceptable as long as at least the four cysteine residues (Cys30, Cys32, Cys55, and Cys71 in the case of human SDF-1α) are retained, and as long as an identity of not less than 90% is retained compared to the naturally occurring amino acid sequence. The SDF-1 may be derived from a mammal, for example, human or a non-human mammal such as monkey, sheep, cow, horse, pig, dog, cat, rabbit, rat, or mouse. For example, as human SDF-1α, the protein registered in GenBank under the accession number: NP_954637 may be used. As SDF-1β, the protein registered in GenBank under the accession number: NP_000600 may be used.

The SDF-1 to be used may be a commercially available product, may be purified from a natural source, or may be produced by peptide synthesis or a genetic engineering technique.

The SDF-1 is included in the medium at, for example, about 10 ng/ml to about 100 ng/ml.

As the SDF-1, an SDF-1 alternative having an SDF-1-like activity may also be used. Examples of such an SDF-1 alternative include CXCR4 agonists. A low molecular weight compound having a CXCR4 agonist activity or the like may be added to the medium instead of SDF-1.

In the present invention, the medium used for the production of the CD4/CD8 double-positive T cells is not limited. The medium may be prepared by adding a p38 inhibitor and/or SDF-1, and preferably also vitamin C, to a basal medium which is used for culture of animal cells. The type of the vitamin C used in the process of production of the CD4/CD8 double-positive T cells is as described above. The concentration of the vitamin C is, for example, 5 µg/ml to 200 µg/ml. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, OP9 medium, and Neurobasal Medium (Life Technologies), and mixed media thereof. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines.

To the medium to be used for the production of the CD4/CD8 double-positive T cells in the present invention, a cytokine(s) selected from the group consisting of SCF, TPO (thrombopoietin), FLT-3L, and IL-7 may be further added. Their concentrations are, for example, as follows: SCF, 10 ng/ml to 100 ng/ml; TPO, 10 ng/ml to 200 ng/ml; IL-7, 1 ng/ml to 100 ng/ml; FLT-3L, 1 ng/ml to 100 ng/ml.

In the production of the CD4/CD8 double-positive T cells, the hematopoietic progenitor cells may be cultured using feeder cells. However, the hematopoietic progenitor cells are preferably cultured without using feeder cells.

The hematopoietic progenitor cells may be cultured by either adherent culture or suspension culture. This step is preferably carried out by adherent culture. In cases of adherent culture, the culture vessel may be coated. Examples of the coating agent include Matrigel (Niwa A, et al. PLoS One. 6(7): e22261, 2011), collagen, gelatin, laminin, heparan sulfate proteoglycan, RetroNectin, Fc-DLL4, and entactin, and combinations thereof.

In cases where the hematopoietic progenitor cells are obtained by suspension culture of an embryoid body/bodies, it is preferred to carry out adherent culture after dissociating the cells into single cells.

In the present invention, the culture temperature conditions for the culture of the hematopoietic progenitor cells for production of the CD4/CD8 double-positive T cells are not limited. The temperature is, for example, about 37° C. to about 42° C., preferably about 37 to about 39° C. The culture period can be appropriately determined by those skilled in the art by monitoring of the number of CD4/CD8 double-positive T cells and/or the like. The number of days is not limited as long as hematopoietic progenitor cells can be obtained. Examples of the number of days include at least not less than 10 days, not less than 12 days, not less than 14 days, not less than 16 days, not less than 18 days, not less than 20 days, not less than 22 days, and not less than 23 days. The number of days is preferably 23 days.

In the present invention, the CD4/CD8 double-positive T cells obtained may be isolated before use, or may be used as a cell population that also contains another cell species. In cases where the CD4/CD8 double-positive T cells are isolated, the isolation may be carried out using any one index selected from the group consisting of CD4, CD8, CD3, and CD45. The isolation method may be a method well known to those skilled in the art, for example, a method in which the cells are labeled with CD4, CD8, CD3, and CD45 antibodies and then isolated using a flow cytometer, or a method in which the cells are purified using an affinity column or the like to which a desired antigen is immobilized.

Step of Inducing Hematopoietic Progenitor Cells from Pluripotent Stem Cells

The present invention provides a method for producing CD4/CD8 double-positive T cells from pluripotent stem cells. This production method includes the steps of: (1) inducing hematopoietic progenitor cells from pluripotent stem cells; and (2) inducing CD4/CD8 double-positive T cells from the hematopoietic progenitor cells.

The step (2), that is, the step of inducing CD4/CD8 double-positive T cells from the hematopoietic progenitor cells, is as described above. The step (1), that is, the step of inducing hematopoietic progenitor cells from pluripotent stem cells, is described below.

Pluripotent Stem Cells

In the present invention, the pluripotent stem cells are stem cells having pluripotency that allows differentiation into many kinds of cells present in a living body, which stem cells also have the growth ability. The pluripotent stem cells at least include arbitrary cells which can be induced into the hematopoietic progenitor cells used in the present invention. The pluripotent stem cells are preferably derived from a mammal, more preferably derived from human.

Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells"), induced pluripotent stem (iPS) cells, pluripotent stem cells derived from cultured fibroblasts or cord blood, and pluripotent cells derived from bone marrow stem cells (Muse cells). The pluripotent stem cells are preferably iPS cells from the viewpoint of the fact that these cells can be obtained without destroying embryos, eggs, or the like during the production process. The pluripotent stem cells are more preferably human iPS cells.

Methods for producing iPS cells are known in the art. These cells can be produced by introducing reprogramming factors into arbitrary somatic cells. Examples of the reprogramming factors herein include genes such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1, and gene products thereof. These reprogramming factors may be used individually, or may be used in combination. Examples of the combination of the reprogramming factors include those described in WO 2007/069666; WO 2008/118820; WO 2009/007852; WO 2009/032194; WO 2009/058413; WO 2009/057831; WO 2009/075119; WO 2009/079007; WO 2009/091659; WO 2009/101084; WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; Huangfu D, et al. (2008), Nat. Biotechnol., 26: 795-797; Shi Y. et al. (2008), Cell Stem Cell, 2: 525-528; Eminli S, et al. (2008), Stem Cells. 26:2467-2474; Huangfu D, et al. (2008), Nat. Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat. Cell Biol. 11:197-203; R. L. Judson et al. (2009), Nat. Biotechnol., 27:459-461; Lyssiotis C A, et al. (2009), Proc Natl Acad Sci USA. 106:8912-8917; Kim J B, et al. (2009), Nature. 461:649-643; Ichida J K. et al. (2009), Cell Stem Cell. 5:491-503; Heng J C, et al. (2010), Cell Stem Cell. 6:167-74; Han J, et al. (2010), Nature. 463:1096-100; Mali P. et al. (2010), Stem Cells. 28:713-720; and Maekawa M, et al. (2011), Nature. 474:225-9.

Examples of the somatic cells include, but are not limited to, any of fetal somatic cells, neonatal somatic cells, and mature, healthy or diseased somatic cells, as well as any of primary cultured cells, subcultured cells, and established cell lines. Specific examples of the somatic cells include: (1) tissue stem cells (somatic stem cells) such as neural stem cells, hematopoietic stem cells, mesenchymal stem cells, and dental pulp stem cells; (2) tissue progenitor cells; and (3) differentiated cells such as blood cells (peripheral blood cells, cord blood cells, and the like), lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells, and adipocytes.

It has been thought that use of T cells as the somatic cells is preferred for the purpose of producing CD4/CD8-positive T cells. However, in the present invention. CD4/CD8-positive T cells can be produced also from iPS cells obtained using non-T-cells as the somatic cells.

In the present invention, the mammalian individual from which the somatic cells are collected is not limited. The mammalian individual is preferably human. In cases where CD4/CD8-positive T cells or CD8-positive T cells prepared by the present invention are used for blood transfusion, the somatic cells as the origin of the iPS cells are preferably isolated from the subject for which the blood transfusion is carried out, from the viewpoint of easily matching the type of the human leukocyte antigen (HLA) with that of the patient for which the blood transfusion is carried out.

In the present invention, the iPS cells used for the induction of the hematopoietic progenitor cells may be iPS cells in which a chimeric antigen receptor (CAR) is introduced. The "chimeric antigen receptor (CAR)" herein means a fusion protein containing an extracellular domain that binds to an antigen, and an intracellular domain derived from a polypeptide different from the extracellular domain. Examples of the chimeric antigen receptor include fusion proteins prepared by linking the antigen recognition site (the L-chain and the H-chain in the variable region) of an antibody against a particular antigen to the intracellular domain of a T-cell receptor such as CD3 and to the intracellular domain of a costimulatory molecule such as CD28 or 4-1BB (for example, Japanese Translated PCT Patent Application Laid-open No. 2015-509716).

The antigen recognition site of the CAR may be selected depending on the target antigen and, by this. T cells specific to the target antigen can be prepared. For example, in cases where the antigen is CD19, the antigen recognition site of an anti-CD19 antibody may be cloned and linked to the intracellular domain of a CD3 molecule to provide a CAR (for example, Cancer Res 2006; 66:10995-11004). By selecting the type(s) and the number(s) of the costimulatory molecule(s) to be linked, the intensity and the duration of the activation can be controlled (for example, Mol Ther. 2009; 17:1453-1464).

By the introduction of the CAR, specificity to the target antigen can be given either to T cells whose differentiation was induced from iPS cells derived from T cells, or to T cells whose differentiation was induced from iPS cells that have not been derived from T cells. Since the antigen molecule can be directly recognized, high immune response can be induced even against tumors showing decreased expression of HLA class I gene.

Step of Inducing Hematopoietic Progenitor Cells from Pluripotent Stem Cells

The hematopoietic progenitor cells can be preferably produced by culturing pluripotent stem cells in a medium supplemented with vitamin C. The "vitamin C" herein means L-ascorbic acid or a derivative thereof, and the "L-ascorbic acid derivative" means a derivative that becomes vitamin C by enzymatic reaction in vivo. Examples of the L-ascorbic acid derivative include vitamin C phosphate, ascorbic acid glucoside, ascorbyl ethyl, vitamin C ester, ascorbyl tetrahexyldecanoate, ascorbyl stearate, and ascorbyl 2-phosphate 6-palmitate. The vitamin C is preferably vitamin C phosphate. Examples of the vitamin C phosphate include salts of L-ascorbic acid phosphate such as L-ascorbic acid phosphate Na and L-ascorbic acid phosphate Mg. The vitamin C is contained in the medium at a concentration of, for example, 5 µg/ml to 500 µg/ml.

The medium used for the production of the hematopoietic progenitor cells is not limited. The medium may be prepared by adding vitamin C or the like to a basal medium which is used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media thereof. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines.

The medium used for the production of the hematopoietic progenitor cells in the present invention may be further supplemented with a cytokine(s) selected from the group consisting of BMP4 (Bone morphogenetic protein 4), VEGF (vascular endothelial growth factor), bFGF (basic fibroblast growth factor), SCF (Stem cell factor), TPO (thrombopoietin), and FLT-3L (Flt3 Ligand).

Their concentrations are, for example, as follows: BMP4, 1 ng/ml to 100 ng/ml; VEGF, 1 ng/ml to 100 ng/ml; SCF. 10 ng/ml to 100 ng/ml; TPO, 1 ng/ml to 100 ng/ml; FLT-3L, 1 ng/ml to 100 ng/ml; bFGF, 1 ng/ml to 100 ng/ml.

A TGFβ inhibitor may also be added. The TGFβ inhibitor is a low molecular weight inhibitor that interferes with signaling by the TGFβ family, and examples of the TGFβ inhibitor include SB431542 and SB202190 (these are described in R. K. Lindemann et al., Mol. Cancer 2:20 (2003)), SB505124 (GlaxoSmithKline), NPC30345, SD093, SD908, SD208 (Scios), LY2109761, LY364947, and LY580276 (Lilly Research Laboratories). For example, in cases where the TGFβ inhibitor is SB431542, its concentration in the medium is preferably 0.5 µM to 100 µM.

The pluripotent stem cells may be co-cultured with feeder cells such as C3H10T1/2 (Takayama N., et al. J Exp Med. 2817-2830, 2010) or stromal cells derived from a different species (Niwa A et al. J Cell Physiol. 2009 November; 221(2): 367-77). In the present invention, however, the culture is preferably carried out without using feeder cells.

In the production of the hematopoietic progenitor cells in the present invention, the culture method for the pluripotent stem cells may be either adherent culture or suspension culture. Suspension culture is preferred. For example, the pluripotent stem cells may be cultured to 80% confluence on the dish used, and then the resulting colonies may be isolated and dissociated into single cells, followed by subjecting the cells to suspension culture. Examples of the method of the separation of the pluripotent stem cells include a method by mechanical separation, and a separation method using a separation solution having the protease activity and the collagenase activity (e.g., Accutase (trademark) or Accumax (trademark)) or a separation solution having only the collagenase activity.

The "suspension culture" means culturing of cells in a state where the cells are not adhering to the culture vessel. The culture vessel that may be used is not limited, and examples of the culture vessel include culture vessels that are not artificially treated for the purpose of enhancing adhesiveness to cells (for example, by coating treatment with an extracellular matrix or the like), and culture vessels that are artificially treated such that adhesion is suppressed (for example, by coating treatment with polyhydroxyethylmethacrylate (poly-HEMA) or with a nonionic surfactant polyol (e.g., Pluronic F-127)). The suspension culture is preferably carried out while allowing formation of an embryoid body/bodies (EB(s)).

In the present invention, the hematopoietic progenitor cells can also be prepared from a net-like structure (which is also referred to as ES-sac or iPS-sac) obtained by culture of pluripotent stem cells. The "net-like structure" herein is a three-dimensional sac-shaped structure (having a space therein) derived from pluripotent stem cells. The structure is formed with an endothelial cell population and/or the like, and contains hematopoietic progenitor cells therein.

In the present invention, the temperature conditions for the culture for production of the hematopoietic progenitor cells are not limited. The temperature is, for example, about 37° C. to about 42° C., preferably about 37° C. to about 39° C. The culture period can be appropriately determined by those skilled in the art by monitoring of the number of hematopoietic progenitor cells and/or the like. The number of days is not limited as long as hematopoietic progenitor cells can be obtained. Examples of the number of days include at least not less than 6 days, not less than 7 days, not less than 8 days, not less than 9 days, not less than 10 days, not less than 11 days, not less than 12 days, not less than 13 days, and not less than 14 days. The number of days is preferably 14 days. A longer culture period is not problematic in the production of the hematopoietic progenitor cells. The culture may be carried out under hypoxic conditions. Examples of the hypoxic conditions in the present invention include oxygen concentrations of 15%, 10%, 9%, 8%, 7%, 6%, and 5%, and oxygen concentrations lower than these.

Step of Inducing CD8-Positive T Cells from CD4/CD8 Double-Positive T Cells

In the present invention, CD8-positive T cells can be induced from the thus obtained CD4/CD8-positive T cells.

The "CD8-positive T cells" means T cells positive for the surface antigen CD8 (CD8$^+$CD4$^-$). These cells are also called cytotoxic T cells. Since T cells can be recognized by the fact that they are positive for the surface antigens CD3 and CD45, CD8-positive T cells can be identified as cells positive for CD8, CD3, and CD45, and negative for CD4.

In the present invention, the CD8-positive T cells can be produced by a method comprising the step of culturing CD4/CD8 double-positive T cells in a medium supplemented with an adrenocortical hormone agent.

The adrenocortical hormone agent is a glucocorticoid or a derivative thereof, and examples of the adrenocortical hormone agent include cortisone acetate, hydrocortisone, fludrocortisone acetate, prednisolone, triamcinolone, methylprednisolone, dexamethasone, betamethasone, and beclomethasone dipropionate. Dexamethasone is preferred. In cases where the adrenocortical hormone agent is dexamethasone, its concentration in the medium is, for example, 1 nM to 100 nM.

The medium used for the production of the CD8-positive T cells is not limited. The medium may be prepared by adding an adrenocortical hormone agent to a basal medium which is used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media thereof. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines.

In the present invention, the medium used for the production of the CD8-positive T cells preferably further contains an anti-CD3 antibody, vitamin C, and cytokine. Examples of the cytokine include IL-2 and IL-7.

The anti-CD3 antibody is not limited as long as it is an antibody that specifically recognizes CD3. Examples of the anti-CD3 antibody include the antibody produced from OKT3 clone. The concentration of the anti-CD3 antibody in the medium is, for example, 10 ng/ml to 100 ng/ml.

In the present invention, the vitamin C to be used for the production of the CD8-positive T cells can be used under the same conditions as described above.

The concentrations of the components used for the production of the CD8-positive T cells in the medium in the present invention are, for example, as follows: IL-2, 10 U/ml to 1000 U/ml; IL-7, 1 ng/ml to 100 ng/ml.

In the present invention, the culture temperature conditions for the culture of the CD4/CD8 double-positive T cells for the production of the CD8-positive T cells are not limited. The temperature is, for example, about 37° C. to about 42° C., preferably about 37° C. to about 39° C. The culture period can be appropriately determined by those skilled in the art by monitoring of the number of CD8-positive T cells and/or the like. The number of days is not limited as long as hematopoietic progenitor cells can be obtained. Examples of the number of days include at least not less than 1 day, not less than 2 days, not less than 3 days, not less than 4 days, and not less than 5 days. The number of days is preferably 3 days.

Cell Preparation

The present invention provides a cell preparation containing CD4/CD8 double-positive T cells and/or CD8-positive T cells produced by the method described above.

Since the cell preparation of the present invention can produce antigen-specific cytotoxic activity, it can be favorably used for cancer therapy, immune replacement therapy, and the like.

Examples of the method for administration of the cell preparation of the present invention to a patient include a method in which the produced CD4/CD8 double-positive T cells and/or CD8-positive T cells are suspended in physiological saline or the like, and the resulting suspension is directly transplanted to an affected area of the patient, and a method in which the cells are intravenously injected.

The present invention is described below more concretely by way of Examples, but the scope of the present invention is not limited to the Examples.

EXAMPLES iPS cells (the TKT3v 1-7 line, the H25-4 line, and the H25-31 line) were established using the method described in Nishimura T. et al., Cell Stem Cell. 12(1): 114-126, 2013, from human CD3-positive T cells isolated with informed consent.

iPS cells (the Ffl-01 line and the Ffl-14 line) were established by the method described in Nakagawa M, et al., Sci Rep. 4: 3594 (2014) (derived from mononuclear cells in peripheral blood (excluding T cells and B cells)). The Ffl-14 line and the Ffl-01 line are separate clones established from the same donor.

iPS cells (the GPC3 #16 line) were established using the method described in Nishimura T. et al., Cell Stem Cell.

12(1): 114-126, 2013, from antigen-specific T lymphocytes isolated from peripheral blood mononuclear cells.

iPS cells (the Ff-I01 GC33 line) were prepared by introduction of a chimeric antigen receptor (CAR) to the Ff-I01 line using a virus vector. The CAR was prepared by cloning the antigen recognition site of an anti-CD19 antibody, and linking the antigen recognition site to the intracellular domain of the CD3 molecule.

ES cells (the KhES-3 line) were obtained from Institute for Frontier Medical Sciences, Kyoto University.

Example 1

On an ultralow-adhesion-treated 6-well plate (CORNING: #3471). TkT3V1-7. Ffl-01, Ffl-14, or KhES-3 was plated at $3 \times 10^5$ to $6 \times 10^5$ cells/well (Day 0), and the cells were cultured under hypoxic conditions (5% $O_2$) for five days in EB medium (StemPro34 supplemented with 10 μg/ml human insulin, 5.5 μg/ml human transferrin, 5 ng/ml sodium selenite, 2 mM L-glutamine, 45 mM α-monothioglycerol, and 50 μg/ml ascorbic acid) supplemented with 10 ng/ml BMP4, 5 ng/ml bFGF, 15 ng/ml VEGF, and 2 μM SB431542 (Day 5).

Subsequently, 50 ng/ml SCF, 30 ng/ml TPO, and 10 ng/ml Flt3L were added, and additional culture was performed for 5 to 9 days (up to Day 14).

The obtained hematopoietic progenitor cells were cultured for 21 days in OP9 medium (15% FBS, 2 mM L-glutamine. 100 Uml penicillin, 100 ng/ml streptomycin, 55 μM 2-mercaptoethanol, 50 μg/ml ascorbic acid, 10 μg/ml human insulin, 5.5 μg/ml human transferrin. 5 ng/ml sodium selenite) supplemented with 50 ng/ml SCF, 50 ng/ml IL-7, 50 ng/ml Flt3L, 100 ng/ml TPO, 15 μM SB203580 (Tocris Bioscience), and 30 ng/ml SDF-1α (PeproTech), on a 48-well plate coated with Fc-DLL4 (5 μg/ml) (Sino Biological Inc.) and Retronectin (5 μg/ml) (Takara Bio Inc.) (Day 35).

On Day 35, the CD45(+), CD3(+), CD4(+), and CD8(+) fraction was isolated using FACS, to obtain CD4/CD8 double-positive cells (which are referred to as DP cells).

Figure 2:
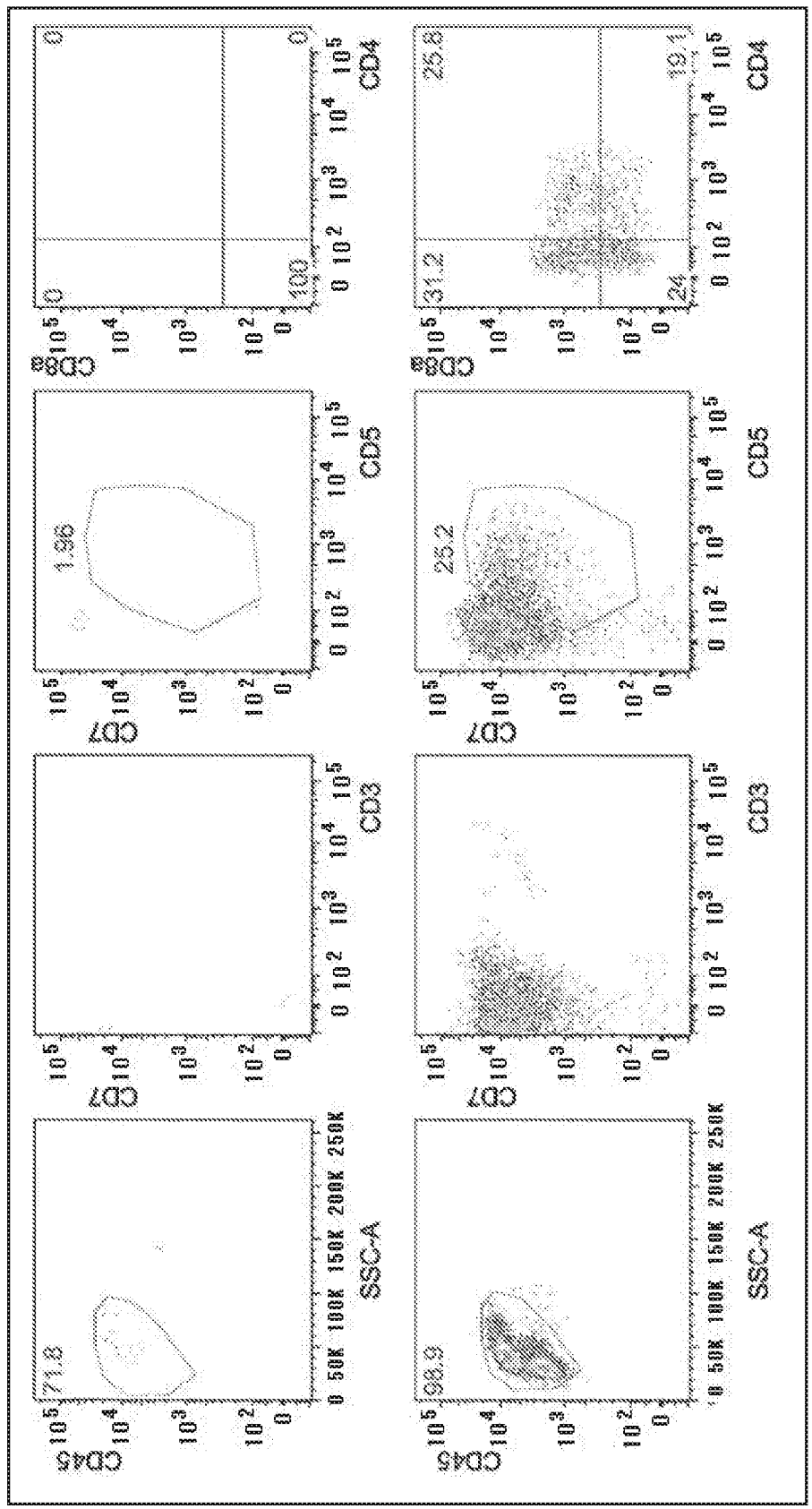
FIG. 2 shows the results of flow cytometry of cells obtained by differentiation induction from iPS cells (Ffl-01). From left to right, diagrams developed for the staining intensities of CD45 and SSC, diagrams developed for the staining intensities of CD7 and CD3, diagrams developed for the staining intensities of CD7 and CD5, and diagrams developed for the staining intensities of CD8 and CD4 are shown. The top row shows the results obtained for a case where neither SB203580 nor SDF-1α was added, and the bottom row shows the results obtained for a case where SB203580 and SDF-1α were added.
Figure 3:
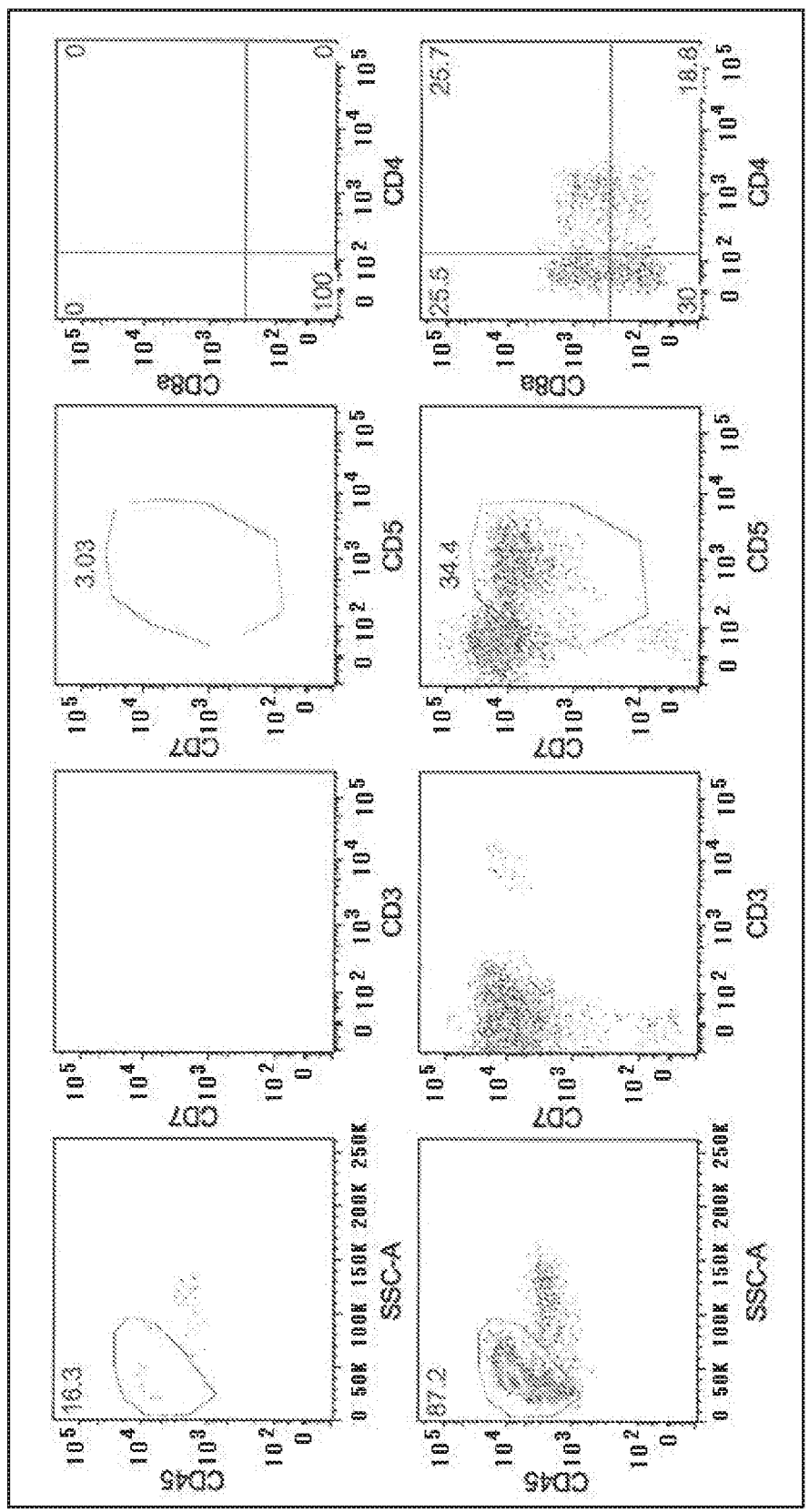
FIG. 3 shows the results of flow cytometry of cells obtained by differentiation induction from iPS cells (Ffl-14). From left to right, diagrams developed for the staining intensities of CD45 and SSC, diagrams developed for the staining intensities of CD7 and CD3, diagrams developed for the staining intensities of CD7 and CD5, and diagrams developed for the staining intensities of CD8 and CD4 are shown. The top row shows the results obtained for a case where neither SB203580 nor SDF-1a was added, and the bottom row shows the results obtained for a case where SB203580 and SDF-1α were added.
Figure 4:
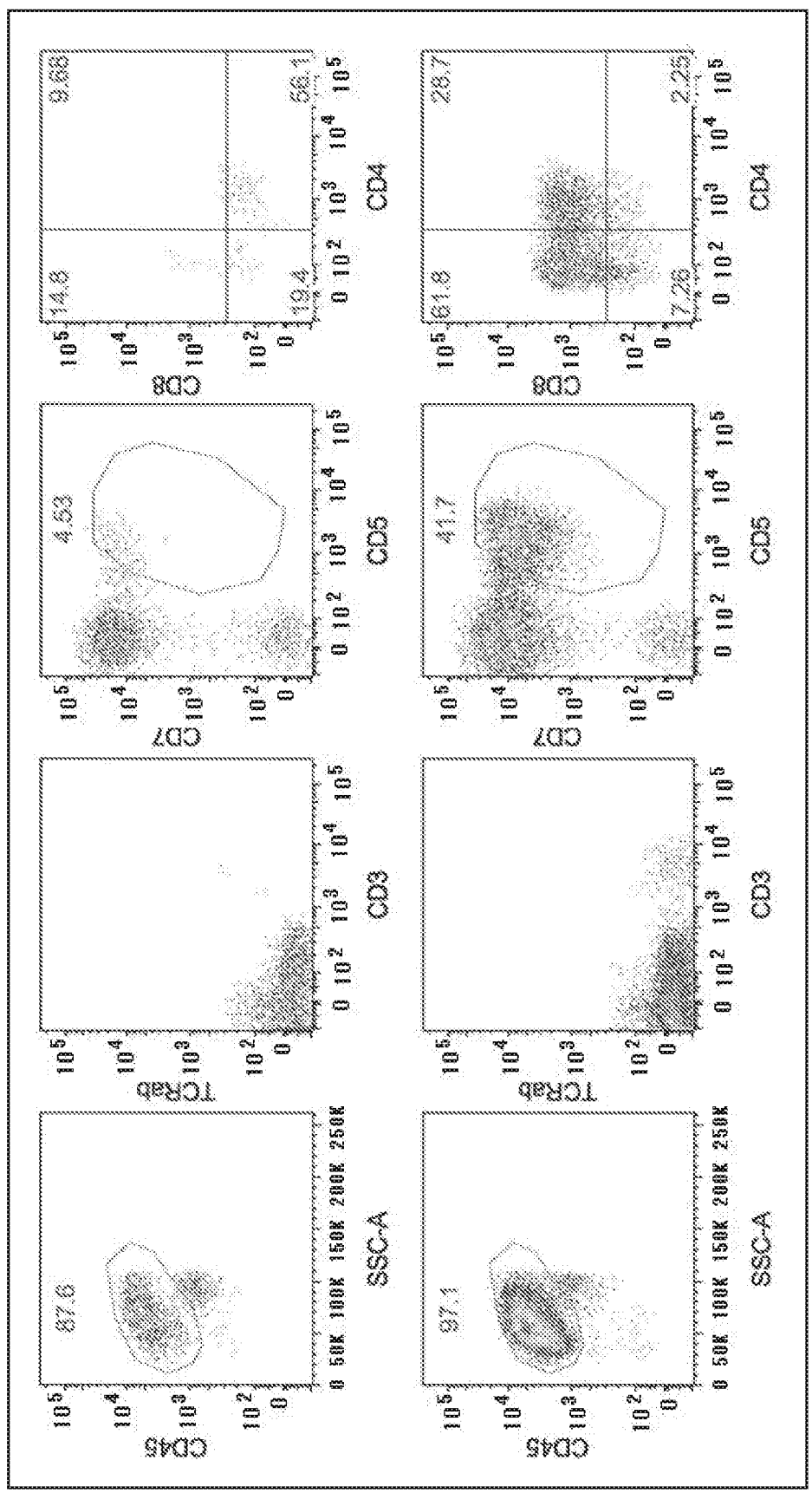
FIG. 4 shows the results of flow cytometry of cells obtained by differentiation induction from ES cells (KhES-3). From left to right, diagrams developed for the staining intensities of CD45 and SSC, diagrams developed for the staining intensities of TCRab and CD3, diagrams developed for the staining intensities of CD7 and CD5, and diagrams developed for the staining intensities of CD8 and CD4 are shown. The top row shows the results obtained for a case where neither SB203580 nor SDF-1α was added, and the bottom row shows the results obtained for a case where SB203580 and SDF-1α were added.

The results are shown in FIG. 1 (TKT3v 1-7), FIG. 2 (Ffl-01). FIG. 3 (Ffl-14), and FIG. 4 (KhES-3). In each figure, the top row shows the results obtained when neither SB203580 nor SDF-1α was added for culture of the hematopoietic progenitor cells. From these results, it was found that CD4/CD8 double-positive T cells can be efficiently obtained by inducing hematopoietic progenitor cells from pluripotent stem cells such as iPS cells or ES cells, and culturing the resulting hematopoietic progenitor cells in a medium containing a p38 inhibitor and SDF-1.

Figure 5:
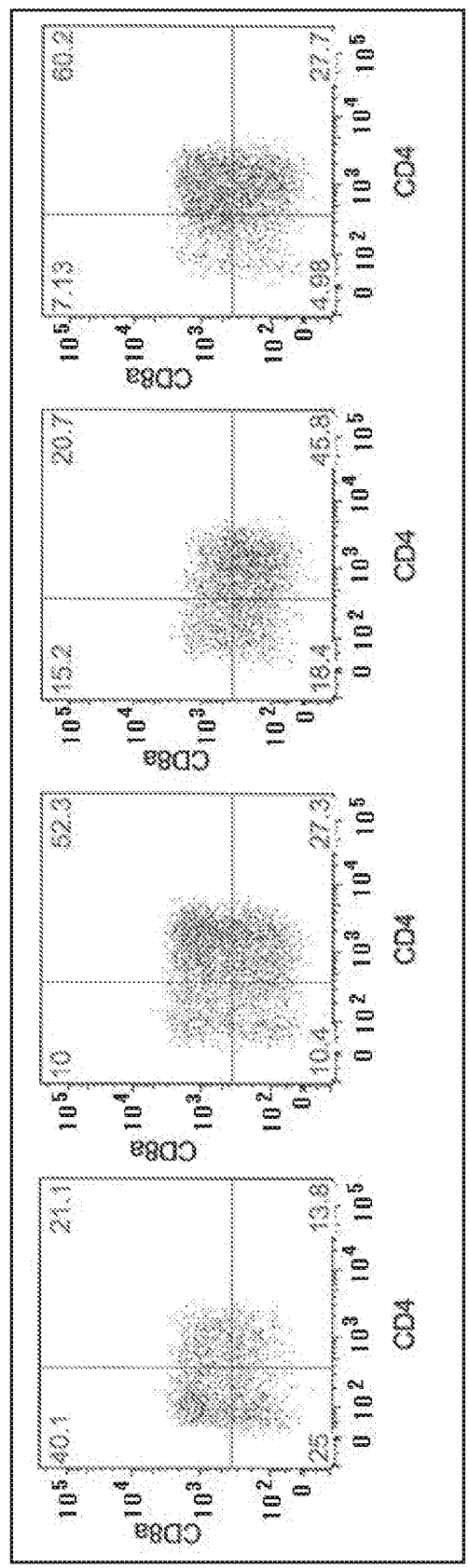
FIG. 5 shows the results of flow cytometry of cells obtained by differentiation induction from iPS cells (TkT3V1-7) (diagrams developed for the staining intensities of CD8 and CD4). From left to right, the result obtained for a case where neither SB203580 nor SDF-1α was added, the result obtained for a case where SB203580 was added, the result obtained for a case where SDF-1α was added, and the result obtained for a case where SB203580 and SDF-1α were added are shown.

By the same procedure as described above, the TKT3v 1-7 line was cultured in each of a medium containing neither SB203580 nor SDF-1α, a medium containing SB203580, a medium containing SDF-1α, and a medium containing SB203580 and SDF-1α. As a result, it was found that the effect of the p38 inhibitor and SDF-1 can be produced even when each of these was used alone (FIG. 5).

Example 2

Figure 6:
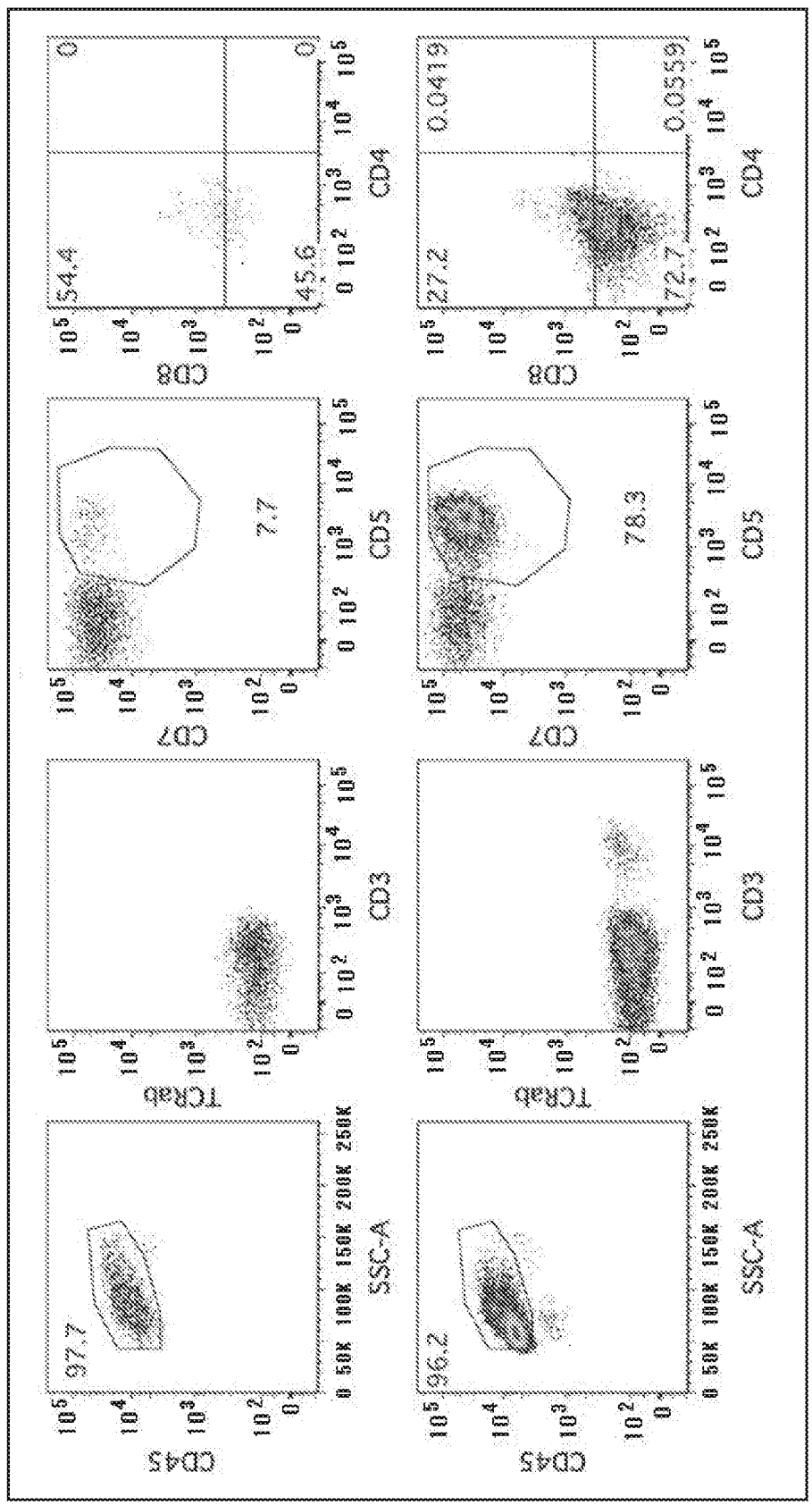
FIG. 6 shows the results of flow cytometry of cells obtained by differentiation induction from CD34-positive cells derived from cord blood (CBCD34+). The top row shows the results obtained for a case where neither SB203580 nor SDF-1α was added, and the bottom row shows the results obtained for a case where SB203580 and SDF-1α were added.

Similarly to the hematopoietic progenitor cells derived from iPS cells in Example 1, CD34-positive hematopoietic progenitor cells derived from cord blood (HemaCare Corporation #CBCD34C-1) were cultured for 21 days in OP9 medium supplemented with 50 ng/ml SCF, 50 ng/ml IL-7, 50 ng/ml Flt3L, 100 ng/ml TPO, 15 M SB203580, and 30 ng/ml SDF-1α, on a 48-well plate coated with Fc-DLL4 (5 μg/ml) and Retronectin (5 μg/ml) (Day 35). On Day 35, the CD45(+), CD3(+), CD4(+), and CD8(+) fraction was isolated using FACS, to obtain CD4/CD8 double-positive cells (which are referred to as DP cells). The results are shown in FIG. 6. The top row in FIG. 6 shows the results obtained when neither SB203580 nor SDF-1α was added for culture of the hematopoietic progenitor cells. From these results, it was found that, even in cases where CD34-positive hematopoietic progenitor cells derived from cord blood are used, CD4/CD8 double-positive T cells can be efficiently obtained by culture in a medium containing a p38 inhibitor and SDF-1.

Figure 7:
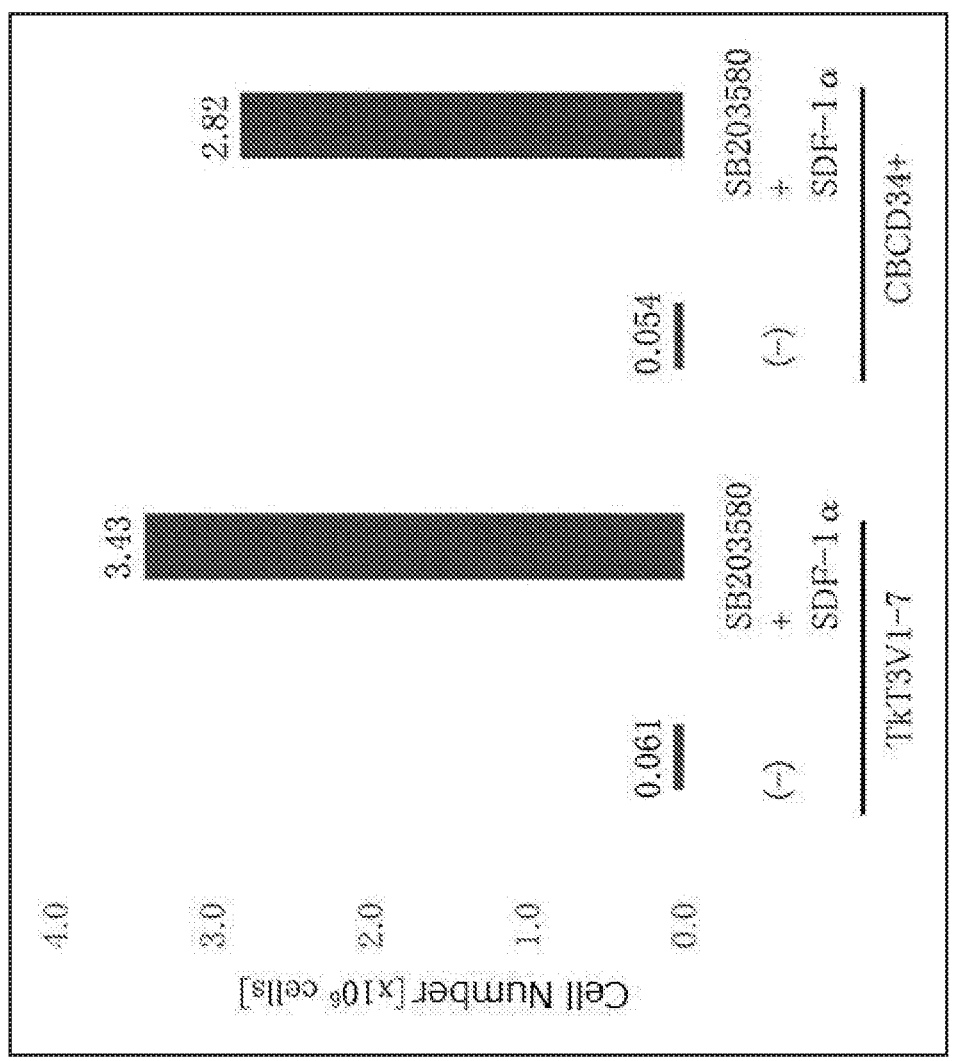
FIG. 7 shows the number of cells obtained by differentiation induction from iPS cells (TkT3V1-7) or CD34-positive cells derived from cord blood (CBCD34+). For each type of cells, the result obtained for a case where neither SB203580 nor SDF-1α was added (−) is shown in the left, and the result obtained for a case where SB203580 and SDF-1α were added is shown in the right.

In Example 1 and Example 2, the total number of cells was counted using a hemacytometer (Wakenbtech Co., Ltd.: #WC2-100) in the FACS analysis (for this value, populations other than CD4/CD8 double-positive cells are also taken into account). As a result, it was found that addition of SB203580 and SDF-1α results in a remarkably increased number of cells in the culture as shown in FIG. 7.

Example 3

Figure 8:
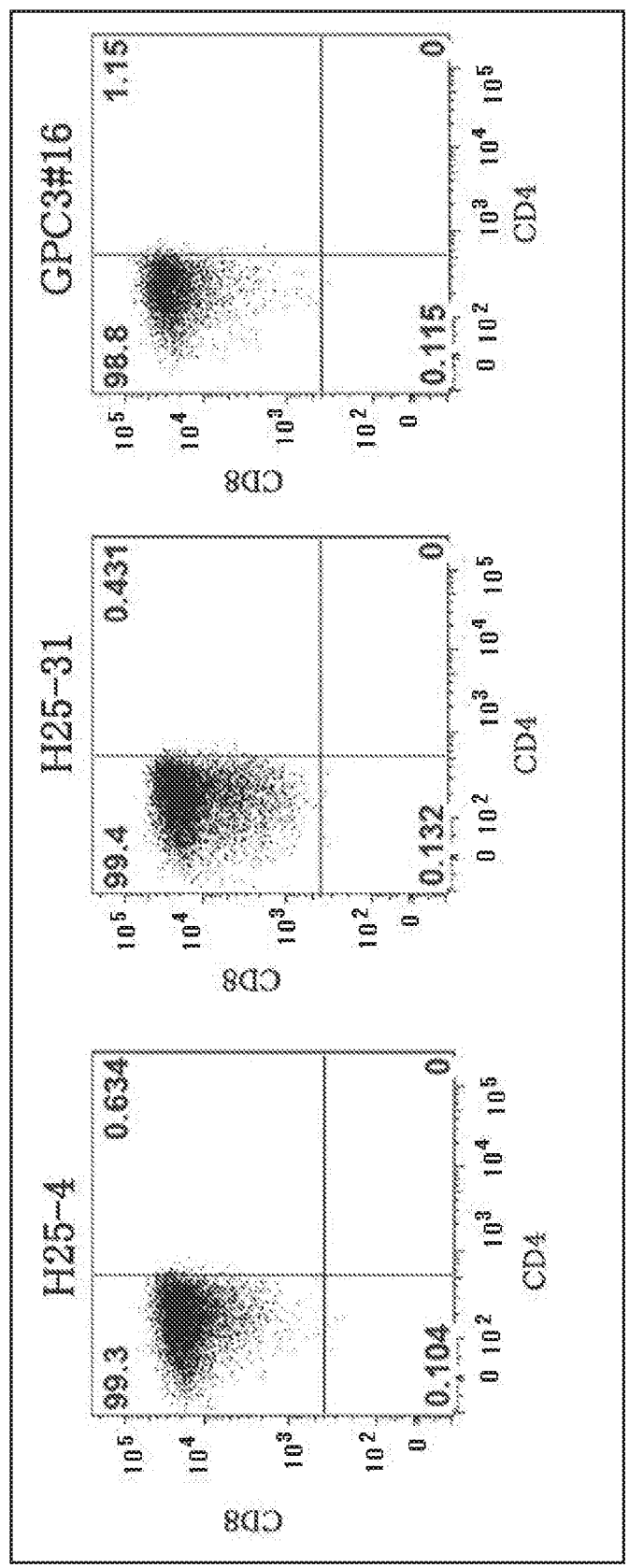
FIG. 8 shows the results of flow cytometry of CD8-positive T cells obtained by differentiation of CD4/CD8 double-positive T cells which were obtained by differentiation induction from iPS cells (H25-4, H25-31, or GPC3 #16).

Using H25-4, H25-31, or GPC3 #16 as iPS cells, culture was performed by the same method as in Example 1 to obtain CD4/CD8 double-positive cells. By stimulating the obtained CD4/CD8 double-positive cells using an anti-CD3 antibody (eBioscience: 16-0037-85) in a medium supplemented with an adrenocortical hormone agent (Fuji Pharma Co., Ltd.: 10171-H02H), CD8-positive T cells (CD8-positive T lymphocytes) could be obtained as shown in FIG. 8.

Figure 9:
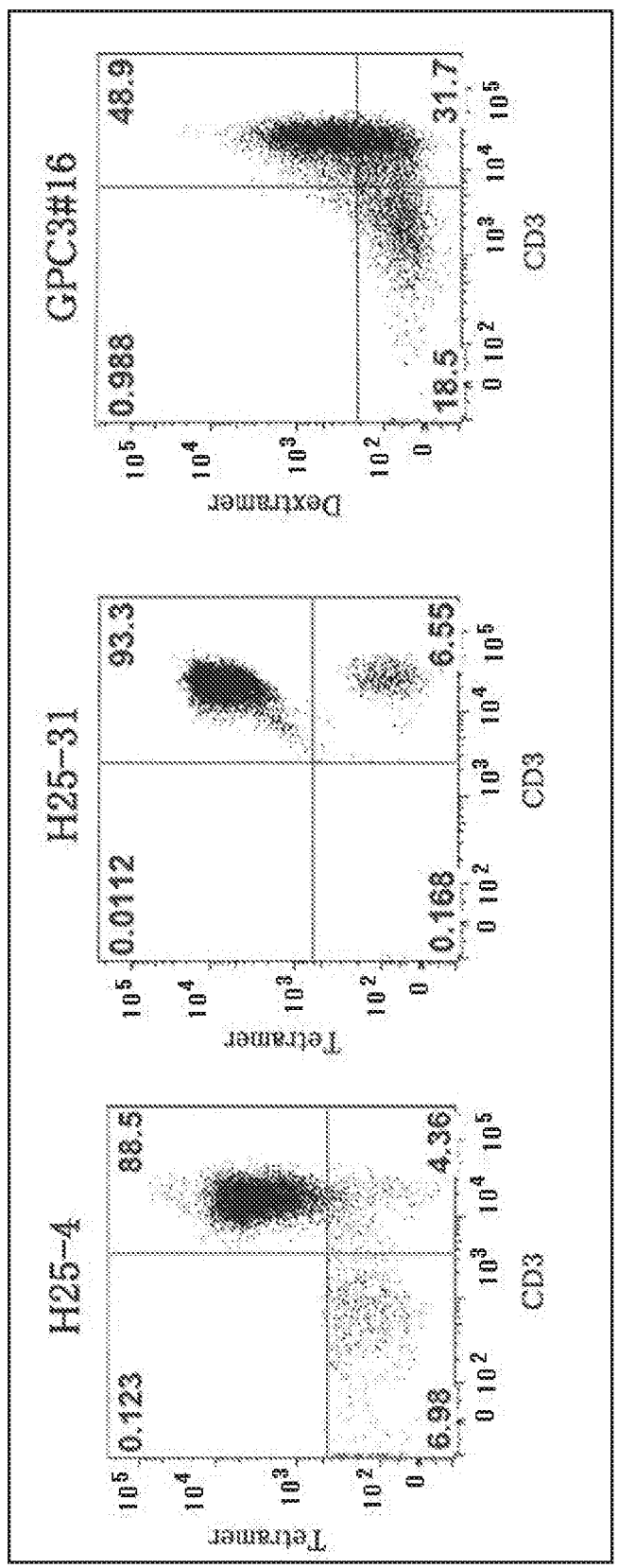
FIG. 9 shows the results of flow cytometry of cells stained with a tetramer (H25-4, H25-31) or a dextramer (GPC3 #16) which is recognized as a specific antigen by the CD8-positive T cells differentiated in FIG. 8.

The obtained CD8-positive T lymphocytes were stained with a tetramer (H25-4, H25-31) or a dextramer (GPC3 #16) which is specifically recognized by each type of T cell receptor and to which the T cell receptor binds, and then FACS analysis was carried out. As a result, as shown in FIG. 9, the CD8-positive T cells obtained as described above were found to have reactivity with the specific antigens.

Figure 10:
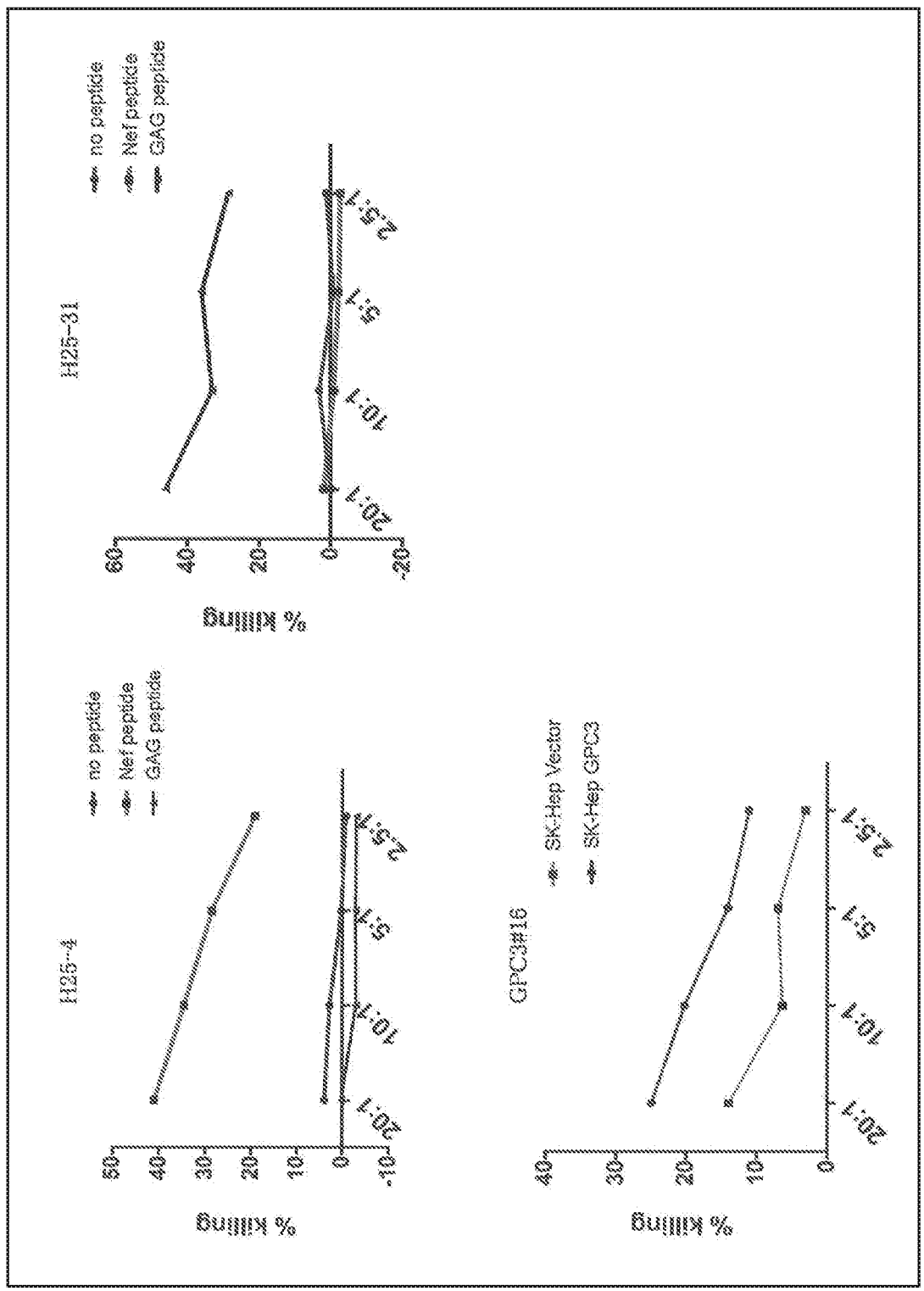
FIG. 10 shows the results of antigen-specific cytotoxicity tests for the CD8-positive T cells obtained in FIG. 8. The results on the cytotoxicity (killing) observed in the absence of a specific antigen (no peptide, SK-Hep Vector), in the presence of a negative control antigen (GAG peptide), or in the presence of a specific antigen (Nef peptide. SK-Hep GPC3) are shown.

The CD8-positive T lymphocytes obtained as described above were co-cultured with a cancer cell line expressing an antigen specifically recognized by each type of CD8-positive T lymphocytes, and the immunoreactivity was evaluated by a $^{51}Cr$ release assay. As a result, as shown in FIG. 10, the H25-4 line and the H25-31 line were found to show cytotoxic immune response specifically and highly efficiently against the cancer cell lines presenting a peptide (Nef or GAG) specifically recognized by these lines. The GPC3 #16 line was found to show high cytotoxic immune response against the cancer cell line that was made to express the GPC3 antigen by gene transfer.

Example 4

Figure 11:
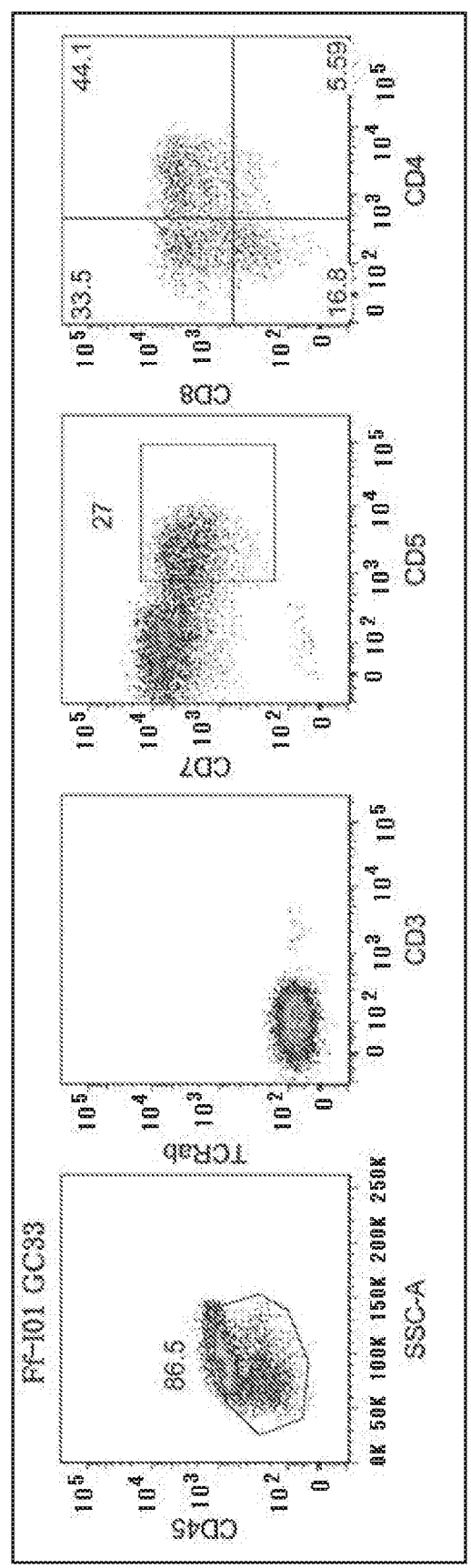
FIG. 11 shows the results of flow cytometry of cells obtained by differentiation induction from iPS cells (the Ff-I01 GC33 line, which is prepared by introduction of an artificial antigen receptor (CAR) into the Ff-I01 line).

Using, as iPS cells, the Ff-I01 GC33 line, which was prepared by introducing the artificial antigen receptor (CAR) into the Ff-I01 line, culture was performed by the same method as in Example 1 to obtain CD4/CD8 double-positive cells. As a result, as shown in FIG. 11, it was found that, also by use of iPS cells having a CAR introduced therein, CD4/CD8 double-positive cells can be efficiently obtained by culture in a medium containing SB203580 and SDF-1.

The invention claimed is:

1. A method for producing CD4/CD8 double-positive T cells, the method comprising the step of culturing hematopoietic progenitor cells in a medium containing a p38 inhibitor and SDF-1 and further containing a delta ligand, SCF, TPO, FLT-3L, and IL-7 to induce CD4/CD8 double-positive T cells, wherein the step is carried out by adherent culture.

2. The method according to claim 1, wherein the p38 inhibitor is SB203580.

3. The method according to claim 1, wherein, in the step, the medium contains vitamin C.

4. The method according to claim 1, wherein the hematopoietic progenitor cells are cultured without using feeder cells.

5. The method according to claim 1, wherein the hematopoietic progenitor cells are hematopoietic progenitor cells differentiated from pluripotent stem cells.

6. The method according to claim 5, wherein the pluripotent stem cells are induced pluripotent stem cells.

7. The method according to claim 6, wherein the induced pluripotent stem cells are derived from somatic cells other than T cells.

8. The method according to claim 6, wherein the induced pluripotent stem cells are induced pluripotent stem cells having a chimeric antigen receptor introduced therein.

9. A method for producing CD4/CD8 double-positive T cells wherein the step is carried out by adherent culture, comprising the steps of:

(1) culturing pluripotent stem cells in a medium to induce hematopoietic progenitor cells; and (2) culturing the hematopoietic progenitor cells obtained in the step (1) in a medium containing a p38 inhibitor and SDF-1 and further containing a delta ligand, SCF, TPO, FLT-3L, and IL-7 to induce CD4/CD8 double-positive T cells.

10. The method according to claim 9, wherein the p38 inhibitor is SB203580.

11. The method according to claim 9, wherein the step (1) is carried out by suspension culture.

12. The method according to claim 9, wherein, in the steps (1) and (2), the medium contains vitamin C.

13. The method according to claim 9, wherein, in the steps (1) and (2), the culture is carried out without using feeder cells.

14. The method according to claim 9, wherein the pluripotent stem cells are induced pluripotent stem cells.

15. The method according to claim 14, wherein the induced pluripotent stem cells are derived from somatic cells other than T cells.

16. The method according to claim 14, wherein the induced pluripotent stem cells are induced pluripotent stem cells comprising a transgene encoding a chimeric antigen receptor.

* * * * *